United States Patent
Matsuzaki

(10) Patent No.: US 7,176,328 B2
(45) Date of Patent: Feb. 13, 2007

(54) METHOD OF PRODUCING GLYCIDYL METHACRYLATE

(75) Inventor: Taiji Matsuzaki, Niigata (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 11/268,583

(22) Filed: Nov. 8, 2005

(65) Prior Publication Data

US 2006/0111576 A1   May 25, 2006

(30) Foreign Application Priority Data

Nov. 8, 2004   (JP) ............................. 2004-323915

(51) Int. Cl.
*C07C 69/52* (2006.01)
*C07D 30/27* (2006.01)

(52) U.S. Cl. ...................................... 560/224; 549/515

(58) Field of Classification Search ................ 560/224; 549/515

See application file for complete search history.

(56) References Cited

U.S. PATENT DOCUMENTS 5,380,884 A * 1/1995 Hosokawa et al. ......... 549/515

* cited by examiner

*Primary Examiner*—Samuel A Barts
*Assistant Examiner*—Lalitha Nagubandi
(74) *Attorney, Agent, or Firm*—Antonelli, Terry, Stout and Kraus, LLP.

(57) ABSTRACT

In the production of glycidyl methacrylate from an alkali metal salt of methacrylic acid and epichlorohydrin, at least one water-soluble polymerization inhibitor is added at an appropriate stage of the production. The addition of the water-soluble polymerization inhibitor prevents the formation of insoluble solid matters to increase the efficiency of phase separation in the washing operation for removing a by-produced salt and form a clear interface between the phases, thereby minimizing the recovery loss. In addition, the troubles such as clogging of pipe lines of production apparatus and equipment for waster water treatment can be avoided.

5 Claims, No Drawings

METHOD OF PRODUCING GLYCIDYL METHACRYLATE

BACKGROUND OF THE INVENTION

1. Field of the Invention

The present invention relates to a method of producing glycidyl methacrylate (GMA) from an alkali metal salt of methacrylic acid (MAA) and epichlorohydrin (EpCH). GMA is useful as materials for weather-resistant paints and resins.

2. Description of the Prior Art

In one of the known methods of producing GMA, an alkali metal salt of MAA obtained from MAA and an alkali metal compound is allowed to react with EpCH thereby forming GMA (for example, GB 2025970A). In this method, an alkali metal chloride is by-produced in an amount equimolar with GMA. Therefore, water is added to the reaction product liquid to dissolve the by-produced salt, and the water phase is discharged as a waste water after a phase separation. However, in the production of GMA by such a method, the amount of solid matters which are insoluble in both the upper oil phase and the lower water phase is gradually increased during the operation for phase separation. The formed insoluble solid matters make the phase separation incomplete, to cause the loss of useful components because the useful components are discharged together with the aqueous solution of by-produced salt. More disadvantageously, the insoluble solid matters are also formed during the discharge of the aqueous solution of by-produced salt, during its storage and during its transfer, to impede the stable driving of production apparatus and stable production by causing the clogging of transfer pipes and the breakdown of pumps. In addition, the treatment of waste insoluble solid matters is cost-consuming to drastically reduce the cost-effectiveness of the production. Therefore, it has been intensely demanded to develop a method of producing GMA free from the formation of insoluble solid matters during the phase separation and its formation in the separated aqueous solution of by-produced salt.

JP-A-2003-238478 (corresponding to US 2005/0119498A1) discloses a method of producing metal salts of MAA with a reduced amount of water, in which an aqueous solution of an alkali metal salt, alkaline earth metal salt or zinc salt of MAA is heated under reduced pressure in the presence of a water-soluble polymerization inhibitor, to remove the water in the metal salt of MAA by distillation. However, the proposed method relates to the production of metal salt of MAA and the removal of water from the metal salt of MAA. The production of GMA by the reaction of a metal salt of MAA and EpCH, and the problems mentioned above in such a GMA production are not described or considered in the patent document.

SUMMARY OF THE INVENTION

An object of the invention is to solve the above problems in the prior art and to provide a method of producing GMA which is free from the formation of insoluble solid matters during the operation of phase separation and during the storage of separated aqueous solution of by-produced salt.

As a result of extensive research for solving the above problems, the inventor has found that the insoluble solid matters are formed by the polymerization of easily polymerizable compounds such as non-reacted MAA, its alkali metal salts, target GMA, and by-produced vinyl-containing compounds. After further research, it has been found that, upon the addition of water for removal of by-produced salt to the reaction liquid after the synthesis of GMA, the water-insoluble polymerization inhibitor hardly transfers into the water phase, whereas a part of the easily polymerizable compounds mentioned above relatively easily transfers into the water phase. The term "water-soluble" referred to herein means a solubility of one gram or more to 100 g of neutral water at 20° C. From the results of the above researches, it has been deduced that, in the production of GMA using only a known water-insoluble polymerization inhibitor such as phenothiazine and 2,2'-methylenebis(4-methyl-6-t-butylphenol), the polymerization hardly occurs in the oil phase near the interface during the washing of the reaction product liquid with water for removal of by-produced salt, because the oil phase contains the water-insoluble polymerization inhibitor. In contrast, the polymerization easily occurs in the water phase because the polymerization inhibitor is scarcely present in the water phase, to produce insoluble solid matters.

The inventor has searched extensively for a water-soluble polymerization inhibitor which is capable of preventing the above polymerization in the water phase. As a result thereof, water-soluble polymerization inhibitors meeting such a purpose have been found and the present invention has been accomplished on the basis of this finding.

Thus, the present invention relates to a method of producing glycidyl methacrylate including a step of producing glycidyl methacrylate by a reaction of an alkali metal salt of methacrylic acid and epichlorohydrin and a step of removing a by-produced alkali metal chloride by washing with water, the method being performed in the presence of at least one water-soluble polymerization inhibitor.

DETAILED DESCRIPTION OF THE INVENTION

The present invention will described below in detail. The production of GMA from MAA and EpCH is known, and GMA can be produced, for example, by the method of GB 2025970A as described below.

An alkali metal compound in an amount of a neutralization equivalent or more, preferably from about 1.05 to 2 times the neutralization equivalent with respect to MAA to be added is suspended in EpCH, and then, the neutralization of alkali metal compound is performed by gradually adding MAA into the suspension under heating. The heating is conducted so as to maintain the azeotropic distillation of the water generated by the neutralization and EpCH during the addition of MAA. For example, when the reaction is performed under atmospheric pressure, the reaction system is preferably maintained at 90° C. or higher. Although the neutralization may be performed in an inert organic solvent, its use can be omitted because EpCH serves as the solvent. The alkali metal compound is preferably a carbonate or hydrogencarbonate of an alkali metal such as sodium and potassium. The neutralization may be performed in the presence of a known water-insoluble polymerization inhibitor such as phenothiazine and 2,2'-methylenebis(4-methyl-6-t-butylphenol). If used, the amount of the water-insoluble polymerization inhibitor is preferably from 0.01 to 2.0 mol % of MAA.

After the azeotropic distillation of water generated by the neutralization is no longer detected, i.e., after the completion of the neutralization, the reaction between the alkali metal salt of MAA and EpCH (esterification accompanied with the elimination of alkali chloride) is performed in the presence of a catalyst preferably at 90 to 120° C. for 1 to 3 h. The amount of the catalyst is preferably from about 0.01 to 1.5 mol % of MAA.

Known catalysts may be used, and examples thereof, but not limited to, include tertiary amines such as triethylamine, tributylamine, triphenylamine, dimethylaniline and pyridine; and quaternary ammonium salts such as trimethylbenzylammonium chloride, triethylbenzylammonium chloride, tetramethylammonium chloride and tetramethylammonium bromide.

In the production method described above, GMA is obtained in high yields together with the by-production of a slurry alkali metal chloride in nearly the same number of moles as that of GMA. Therefore, the alkali metal chloride should be removed before distilling the reaction product liquid.

The methods of removing the alkali metal chloride may include a filtration, a centrifugal separation, an addition of water, etc., with the addition of water being most preferred because the filtration and centrifugal separation include a complicated treatment of solid residues and the alkali metal chloride is soluble in water.

An amount of water enough to fully dissolve the alkali metal chloride is sufficient. Since GMA and EpCH are slightly soluble in water, however, the addition of an excessively large amount of water is not preferred economically. The amount of water to be added is preferably determined so that the alkali metal chloride is nearly saturated in the water phase.

The kind of water is not critical and any of ion-exchanged water, ordinary tap water, condensed water of steam and by-produced water in the neutralization for converting MAA into the alkali metal salt can be used, with ion-exchanged water being most preferred because the polymerization of GMA is accelerated by metal ions such as iron ion.

Water is added to the reaction product liquid under reduced pressure, atmospheric pressure or application of pressure, with the addition under atmospheric pressure being preferred unless otherwise needed.

In the method of the present invention, a water-soluble polymerization inhibitor is added at any stage of the production of GMA, for example, at the time of charging the starting materials, before the GMA synthesis, during the GMA synthesis, before the addition of water for removing by-produced salt, together with the addition of water, immediately after the addition of water, or to the separated water phase.

The water-soluble polymerization inhibitor is added in an amount of preferably from 10 to 100,000 ppm, and more preferably from 100 to 10,000 ppm of the amount of the added water. If excessively small, the expected effect is not attained sufficiently, and uneconomical if excessively large. The water-soluble polymerization inhibitor is added in a form of solid such as powder and pellet or in a form of aqueous solution.

After the addition of water, the alkali metal chloride is dissolved into water preferably at 20 to 60° C., more preferably at 30 to 50° C. under circulation or stirring. If the temperature is excessively low, the solubility of the alkali metal chloride is lowered to increase the necessary amount of water or make the separation of the water phase and the oil phase unclear. If the temperature is excessively high, an unfavorable side reaction proceeds to likely reduce the yield of GMA. After the alkali metal chloride is dissolved into water, the liquid mixture is allowed to stand for the separation into the oil phase and the water phase. After discharging the water phase, a purified GMA is obtained from the oil phase by purification such as distillation.

The water-soluble polymerization inhibitor is at lease one compound selected from the group consisting of sodium iodide, potassium iodide, ascorbic acid, sodium ascorbate, potassium ascorbate and 4-hydroxy-2,2,6,6-tetramethylpiperidine-1-oxyl (4H-TEMPO). Sodium iodide, potassium iodide and 4H-TEMPO are suitable when the addition at the time of charging the starting materials, before the GMA synthesis or during the GMA synthesis is intended because of their high heat stability.

As described above, the alkali metal compound is used in the GMA synthesis preferably in an amount of about 1.05 to 2.00 times the neutral equivalent to MAA. If ascorbic acid is used as the water-soluble polymerization inhibitor, an alkali metal salt of ascorbic acid is formed by the neutralization with an excessive alkali metal compound. Since the alkali metal salt of ascorbic acid is also effective for inhibiting the polymerization, the formation of insoluble solid matters can be prevented also by the use of ascorbic acid. Ascorbic acid may be used in any forms of L-isomer, D-isomer, racemic form and a mixture of L-isomer and D-isomer in any proportions.

Thus, the polymerization of the easily polymerizable compounds during the phase separation is effectively inhibited by conducting the removal of the by-produced salt in the presence of the water-soluble polymerization inhibitor. By adding the water-soluble polymerization inhibitor into the aqueous solution containing the by-produced salt which is separated after the removal operation of the by-produce salt, the polymerization of the easily polymerizable compounds in the aqueous solution is effectively inhibited. With the method of the invention, the formation of the insoluble solid matters is drastically reduced, to solve the problem of failing to form a clear interface between the oil phase and the water phase and the problem caused by the insoluble solid matters in waste water which are mentioned above.

The present invention will be described in more detail with reference to the following examples and comparative examples. However, it should be noted that the following examples are merely illustrative and the scope of the invention is not limited thereto.

EXAMPLE 1

In a 1-L round flask equipped with a stirrer, a reflux condenser and a decanter, 900 g of EpCH, 58 g of sodium carbonate and one gram of 2,2'-methylenebis(6-t-butyl-4-methylphenol) were stirred under heating. After EpCH began to reflux, 86 g of MAA was added dropwise over one hour. The 0.3 g of tetramethylammonium chloride as a catalyst was added and the reaction was allowed to proceed under reflux for 50 min. After the reaction, the reaction product liquid was cooled to 50° C. and then added with 240 g of ion-exchanged water and 0.5 g of potassium iodide under stirring. The temperature after the addition was 40° C.

The reaction product liquid was subjected to phase separation by being allowed to stand for one hour. No formation of the insoluble solid matters was observed in the discharged water phase even after a 3-day storage at 40° C. The results are shown in Tables 1 and 2.

EXAMPLE 2

The procedure of Example 1 was repeated except for adding 0.6 g of sodium iodide in place of potassium iodide. No formation of the insoluble solid matters was observed in the discharged water phase even after a 3-day storage at 40° C. The results are shown in Table 1.

EXAMPLE 3

The procedure of Example 1 was repeated except for adding 0.3 g of L-ascorbic acid in place of potassium iodide. No formation of the insoluble solid matters was observed in the discharged water phase even after a 3-day storage at 40° C. The results are shown in Table 1.

EXAMPLE 4

The procedure of Example 1 was repeated except for adding 76 g of potassium carbonate in place of sodium carbonate, 306 g of ion-exchanged water, and 0.6 g of L-ascorbic acid in place of potassium iodide. No formation of the insoluble solid matters was observed in the discharged water phase even after a 3-day storage at 40° C. The results are shown in Table 1.

EXAMPLE 5

The procedure of Example 1 was repeated except for adding 0.3 g of sodium L-ascorbate in place of potassium iodide. No formation of the insoluble solid matters was observed in the discharged water phase even after a 3-day storage at 40° C. The results are shown in Table 1.

EXAMPLE 6

The procedure of Example 1 was repeated except for adding 0.1 g of 4H-TEMPO in place of potassium iodide. Although the discharged water phase was colored, no formation of the insoluble solid matters was observed therein even after a 3-day storage at 40° C. The results are shown in Tables 1 and 3.

EXAMPLE 7

The procedure of Example 1 was repeated except for omitting the addition of potassium iodide. The discharged water phase looked turbid in white because of suspended fine particles having a particle size of about 0.1 mm which were hard to sediment. After added with 0.5 g of potassium iodide, the water phase was stored for 3 days at 40° C. The water phase did not become more turbid and no formation of the insoluble solid matters was observed therein. The results are shown in Table 2.

EXAMPLE 8

The procedure of Example 1 was repeated except for adding 0.1 g of 4H-TEMPO simultaneously with the charging of the starting materials in place of adding potassium iodide together with water. Although the discharged water phase was colored, no white solid matter was formed. No formation of the insoluble solid matters was observed therein even after a 3-day storage at 40° C. The results are shown in Table 3.

EXAMPLE 9

The procedure of Example 1 was repeated except for omitting the addition of potassium iodide. The discharged water phase looked turbid in white because of suspended fine particles having a particle size of about 0.1 mm which were hard to sediment. After added with 0.1 g of 4H-TEMPO, the water phase was stored for 3 days at 40° C. The water phase did not become more turbid and no formation of the insoluble solid matters was observed therein. The results are shown in Table 3.

Comparative Example 1

The procedure of Example 1 was repeated except for adding 240 g of ion-exchanged water and omitting the addition of the water-soluble polymerization inhibitor. After mixing under stirring, the reaction product liquid was allowed to stand for phase separation. The water phase containing the by-produced salt looked turbid in white because of suspended fine particles having a particle size of about 0.1 mm. The suspended particles transferred, with the time for standing, into the interface between the water phase and the oil phase containing GMA, to make the phase separation incomplete and prevent the formation of a clear water-to-oil interface. Upon storing the water phase thus incompletely separated for 3 days at 40° C., the formation of white, insoluble membranes having a thickness of about 0.5 mm and an area of 1 cm$^2$ or more was observed near the surface. The results are shown in Tables 1 and 2.

Comparative Example 2

The procedure of Example 1 was repeated except for adding 240 g of ion-exchanged water and adding 1.0 g of phenothiazine in place of potassium iodide. After mixing under stirring, the reaction product liquid was allowed to stand for phase separation. The oil phase was colored in yellow, and the water phase containing the by-produced salt looked turbid in white because of suspended fine particles having a particle size of about 0.1 mm. The suspended particles transferred, with the time for standing, into the interface between the water phase and the oil phase containing GMA, to make the phase separation incomplete and prevent the formation of a clear water-to-oil interface. Upon storing the water phase thus incompletely separated for 3 days at 40° C., the formation of white, insoluble membranes having a thickness of about 0.5 mm and an area of 1 cm$^2$ or more was observed near the surface. The results are shown in Table 1.

Comparative Example 3

The procedure of Example 1 was repeated except for adding 240 g of ion-exchanged water and adding 1.0 g of 2,2'-methylenebis(4-methyl-6-t-butylphenol) in place of potassium iodide. After mixing under stirring, the reaction product liquid was allowed to stand for phase separation. The water phase containing the by-produced salt looked turbid in white because of suspended fine particles having a particle size of about 0.1 mm. The suspended particles transferred, with the time for standing, into the interface between the water phase and the oil phase containing GMA, to make the phase separation incomplete and prevent the formation of a clear water-to-oil interface. Upon storing the water phase thus incompletely separated for 3 days at 40° C., the formation of white, insoluble membranes having a thickness of about 0.5 mm and an area of 1 cm$^2$ or more was observed near the surface. The results are shown in Table 1.

TABLE 1

|  | Examples | | | | | |
| --- | --- | --- | --- | --- | --- | --- |
|  | 1 | 2 | 3 | 4 | 5 | 6 |
| Water-soluble polymerization inhibitor (g) | | | | | | |
| potassium iodide | 0.5 | — | — | — | — | — |
| sodium iodide | — | 0.6 | — | — | — | — |
| L-ascorbic acid | — | — | 0.3 | — | — | — |
| L-ascorbic acid | — | — | — | 0.6 | — | — |
| sodium L-ascorbate | — | — | — | — | 0.3 | — |
| 4H-TEMPO | — | — | — | — | — | 0.1 |
| Water-insoluble polymerization inhibitor (g) | | | | | | |
| phenothiazine | — | — | — | — | — | — |
| MBMBP* | — | — | — | — | — | — |
| Formation of insoluble solid matters after 3-day storage at 40° C. | none | none | none | none | none | none |

TABLE 1-continued

|  | Comparative Examples | | |
| --- | --- | --- | --- |
|  | 1 | 2 | 3 |
| Water-soluble polymerization inhibitor (g) | | | |
| potassium iodide | — | — | — |
| sodium iodide | — | — | — |
| L-ascorbic acid | — | — | — |
| L-ascorbic acid | — | — | — |
| sodium L-ascorbate | — | — | — |
| 4H-TEMPO | — | — | — |
| Water-insoluble polymerization inhibitor (g) | | | |
| phenothiazine | — | 1.0 | — |
| MBMBP* | — | — | 1.0 |
| Formation of insoluble solid matters after 3-day storage at 40° C. | yes | yes | yes |

MBMBP*: 2,2'-methylenebis(4-methyl-6-t-butylphenol)

TABLE 2

|  | Examples | | Comparative |
| --- | --- | --- | --- |
|  | 1 | 7 | example 1 |
| Addition of potassium iodide | together with the addition of water | added to the water phase after discharging | — |
| Appearance of water phase just after discharging | almost clear | turbid in white | turbid in white |
| Appearance of water phase after 3-day storage at 40° C. | almost clear | turbid in white | membrane of solid matter |

TABLE 3

|  | Examples | | | Comparative |
| --- | --- | --- | --- | --- |
|  | 6 | 8 | 9 | example 1 |
| Addition of 4H-TEMPO | together with the addition of water | together with the charge of starting materials | added to the water phase after discharging | — |
| Appearance of water phase just after discharging | almost clear | almost clear | turbid in white | turbid in white |
| Appearance of water phase after 3-day storage at 40° C. | almost clear | almost clear | turbid in white | membrane of solid matter |

Since a water-soluble polymerization inhibitor is used in the production of GMA from an alkali metal salt of MAA and EpCH of the invention, the formation of the insoluble solid matters is prevented in the method of the present invention. Therefore, the separation of the oil phase containing GMA and the water phase containing by-produced salt in the step for removing the by-produced salt by washing with water can be completed. In addition, the trouble such as clogging which may cause a shut-down of apparatus is avoided and GMA can be produced stably with low costs.

What is claimed is:

1. A method of producing glycidyl methacrylate comprising a step of producing glycidyl methacrylate by a reaction of an alkali metal salt of methacrylic acid and epichlorohydrin and a step of removing a by-produced alkali metal chloride by washing with water, the method being performed in the presence of at least one water-soluble polymerization inhibitor.

2. The method according to claim 1, wherein the by-produced alkali metal chloride is removed by washing with water in the presence of said at least one water-soluble polymerization inhibitor.

3. The method according to claim 1, wherein a phase separation is performed after removing the by-produced alkali metal chloride by washing with water, and then a separated water phase is added with said at least one water-soluble polymerization inhibitor.

4. The method according to claim 1, wherein the step of producing glycidyl methacrylate by the reaction of an alkali metal salt of methacrylic acid and epichlorohydrin is performed in the presence of said at least one water-soluble polymerization inhibitor.

5. The method according to claim 1, wherein said at least one water-soluble polymerization inhibitor is selected from the group consisting of sodium iodide, potassium iodide, ascorbic acid, sodium ascorbate, potassium ascorbate, and 4-hydroxy-2,2,6,6-tetramethylpiperidine-1-oxyl.

* * * * *